US010791255B2

United States Patent
Ghofrani et al.

(10) Patent No.: US 10,791,255 B2
(45) Date of Patent: Sep. 29, 2020

(54) CONFIGURABLE OPTICAL BEAM SCAN DRIVE SYTEMS

(71) Applicant: Bioptigen, Inc., Morrisville, NC (US)

(72) Inventors: Mehran Ghofrani, Cary, NC (US); Al-Hafeez Z. Dhalla, Durham, NC (US); Christopher Saxer, Cary, NC (US)

(73) Assignee: Leica Microsystems Inc., Buffalo Grove, IL (US)

( * ) Notice: Subject to any disclaimer, the term of this patent is extended or adjusted under 35 U.S.C. 154(b) by 47 days.

(21) Appl. No.: 15/523,002

(22) PCT Filed: Nov. 6, 2015

(86) PCT No.: PCT/US2015/059445
§ 371 (c)(1),
(2) Date: Apr. 28, 2017

(87) PCT Pub. No.: WO2016/073840
PCT Pub. Date: May 12, 2016

(65) Prior Publication Data
US 2017/0347001 A1 Nov. 30, 2017

Related U.S. Application Data

(60) Provisional application No. 62/076,708, filed on Nov. 7, 2014.

(51) Int. Cl.
*H04N 5/225* (2006.01)
*A61B 3/10* (2006.01)
(Continued)

(52) U.S. Cl.
CPC .......... *H04N 5/2256* (2013.01); *A61B 3/102* (2013.01); *A61B 3/13* (2013.01); *G01B 9/02091* (2013.01); *H04N 2201/0436* (2013.01)

(58) Field of Classification Search
None
See application file for complete search history.

(56) References Cited

U.S. PATENT DOCUMENTS

2010/0268042 A1* 10/2010 Wang .................. A61B 5/0059
600/322
2011/0304819 A1* 12/2011 Juhasz .................. A61B 3/102
351/206
(Continued)

FOREIGN PATENT DOCUMENTS

| CN | 103167851 A | 6/2013 |
| JP | 2011-033467 A | 2/2011 |
| JP | 2014-140489 A | 8/2014 |

OTHER PUBLICATIONS

First Notification of Office Action, Chinese Patent Application No. 201580060513.4, dated Apr. 27, 2018, 13 pages.
(Continued)

*Primary Examiner* — Chikaodili E Anyikire
(74) *Attorney, Agent, or Firm* — Stanek Lemon Crouse & Meeks, PA

(57) ABSTRACT

A scanning optical system is provided including a source of optical radiation; an optical scanning beam delivery system for delivering optical radiation to a subject, wherein the optical scanning beam delivery system includes a plurality of optical elements including at least one steerable mirror; at least one actuator coupled to the at least one steerable mirror; a detection system for detecting optical radiation returned from a subject; a communications device including a user interface and configured to process a set of instructions at least partially responsive to inputs from the user interface; a controller comprising memory, a microcontroller and an field programmable gate array (FPGA), the microcontroller and FPGA receiving instructions derived from the communications device; and at least one actuator coupled to
(Continued)

the at least one steerable mirror. The at least one actuator receives a first instruction set from the microcontroller in the form of sequential commands and a second instruction set from the FPGA in the form of concurrent commands. The first instruction set establishes a pattern of motion of the at least one steerable mirror at least partially responsive to inputs from the user interface of the communications device. The second instruction set modifies an attribute of the pattern of motion of the at least one steerable mirror in substantially real-time at least partially responsive to one or more triggering events.

15 Claims, 13 Drawing Sheets

(51) Int. Cl.
*G01B 9/02* (2006.01)
*A61B 3/13* (2006.01)

(56) References Cited

U.S. PATENT DOCUMENTS

| | | | |
|---|---|---|---|
| 2014/0028997 A1* | 1/2014 | Cable | G01B 9/02091 356/51 |
| 2014/0104618 A1* | 4/2014 | Potsaid | G02B 26/105 356/497 |
| 2014/0316389 A1 | 10/2014 | Schuele et al. | |
| 2016/0338589 A1* | 11/2016 | Carrasco-Zevallos | A61B 3/102 |

OTHER PUBLICATIONS

International Search Report and Written Opinion, PCT/US2015/059445, dated Feb. 25, 2016, 8 pages.
Notification of Reasons for Refusal, Japanese Patent Application No. 2017-523966, dated Jul. 2, 2018, 9 pages.

* cited by examiner

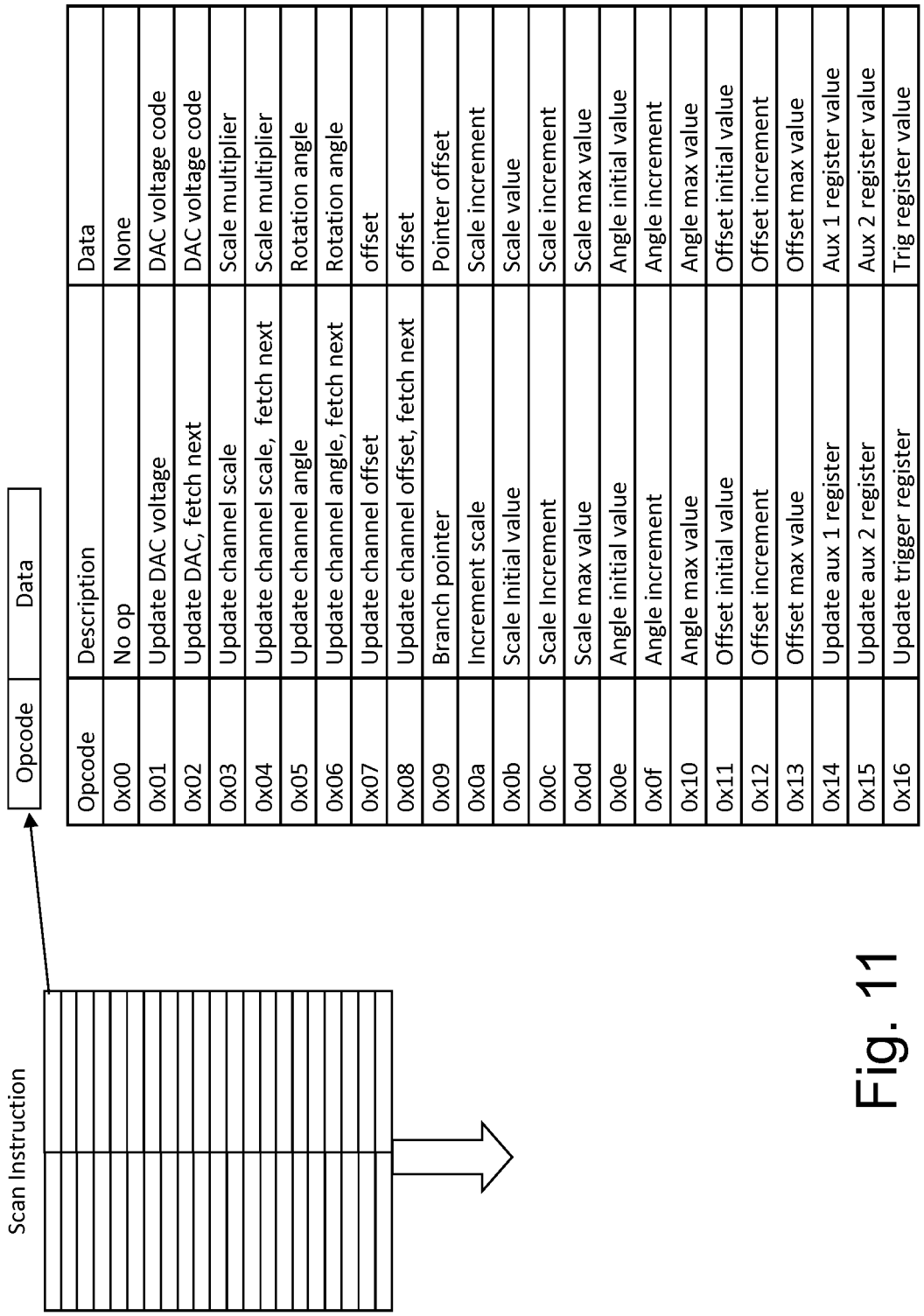

| Opcode | Description | Data |
|---|---|---|
| 0x00 | No op | None |
| 0x01 | Update DAC voltage | DAC voltage code |
| 0x02 | Update DAC, fetch next | DAC voltage code |
| 0x03 | Update channel scale | Scale multiplier |
| 0x04 | Update channel scale, fetch next | Scale multiplier |
| 0x05 | Update channel angle | Rotation angle |
| 0x06 | Update channel angle, fetch next | Rotation angle |
| 0x07 | Update channel offset | offset |
| 0x08 | Update channel offset, fetch next | offset |
| 0x09 | Branch pointer | Pointer offset |
| 0x0a | Increment scale | Scale increment |
| 0x0b | Scale Initial value | Scale value |
| 0x0c | Scale Increment | Scale increment |
| 0x0d | Scale max value | Scale max value |
| 0x0e | Angle initial value | Angle initial value |
| 0x0f | Angle increment | Angle increment |
| 0x10 | Angle max value | Angle max value |
| 0x11 | Offset initial value | Offset initial value |
| 0x12 | Offset increment | Offset increment |
| 0x13 | Offset max value | Offset max value |
| 0x14 | Update aux 1 register | Aux 1 register value |
| 0x15 | Update aux 2 register | Aux 2 register value |
| 0x16 | Update trigger register | Trig register value |

Fig. 11

CONFIGURABLE OPTICAL BEAM SCAN DRIVE SYTEMS

CLAIM OF PRIORITY

The present application is a national phase entry of and claims priority to International Patent Application No. PCT/US2015/059445, filed Nov. 6, 2015, which claims priority to U.S. Provisional Application Ser. No. 62/076,708, filed Nov. 7, 2014, the disclosures of which are hereby incorporated herein by reference as if set forth in its their entireties.

FIELD

This present inventive concept relates generally to optical scanning systems and, more particularly, to optical scanning systems having one or more mirrors used to steer a beam of light to produce a desired pattern for various applications.

BACKGROUND

In an optical beam scanning system, such as an Optical Coherence Tomography (OCT) imaging system, precise synchronization of the mirror positions, camera exposures, and other related devices is typically required in order to ensure accurate imaging of a sample. The mirror position tables, in the form of voltages, are stored in a memory buffer and output sequentially, as in sync with a clock. The synchronization clocks come either from the camera system or from an independent clock source. In some applications it may be necessary to generate triggers to indicate a region of interest (ROI) of the scan pattern, which may or not be sequential or periodic within the scan pattern. Generation of periodic trigger signals can be accomplished by one or more clock dividers on the system clock. However, arbitrary trigger generations will not be trivial with simple clock dividers.

The scan pattern coordinates are typically pre-calculated and stored in a table in the system random access memory (RAM). For patterns, such as raster generation, a position progression is repeated in one dimension as the other dimension is sequentially increased. For example, for a 1000×1000 raster, this would result in one million data points, as the data in one dimension is repeated a 1000 times. Dynamic pattern modification would require generating a new coordinate table and transfer into the drive memory.

SUMMARY

Some embodiments of the present inventive concept provide a scanning optical system including a source of optical radiation; an optical scanning beam delivery system for delivering optical radiation to a subject, wherein the optical scanning beam delivery system includes a plurality of optical elements including at least one steerable mirror; at least one actuator coupled to the at least one steerable mirror; a detection system for detecting optical radiation returned from a subject; a communications device including a user interface and configured to process a set of instructions at least partially responsive to inputs from the user interface; a controller comprising memory, a microcontroller and an field programmable gate array (FPGA), the microcontroller and FPGA receiving instructions derived from the communications device; and at least one actuator coupled to the at least one steerable mirror. The at least one actuator receives a first instruction set from the microcontroller in the form of sequential commands and a second instruction set from the FPGA in the form of concurrent commands. The first instruction set establishes a pattern of motion of the at least one steerable mirror at least partially responsive to inputs from the user interface of the communications device. The second instruction set modifies an attribute of the pattern of motion of the at least one steerable mirror in substantially real-time at least partially responsive to one or more triggering events.

In further embodiments, the microcontroller may be a soft-processor configured within the FPGA.

In still further embodiments, the system may be one of an optical coherence tomography imaging system, a scanning laser ophthalmoscope, and a scanning confocal optical microscope.

In some embodiments, the microcontroller may populate a table in the memory of the controller with the first instruction set.

In still further embodiments, the FPGA may be configured to execute the instructions in the memory of the controller responsive to the second instruction set.

In some embodiments, the second instruction set may execute the first instruction set directly or modify one or more of a scan scale, a scan rotation angle, a scan location, a scan correction to a beam position from optical distortion or scanning system mechanical nonlinearities, a scan start time, a scan stop time, and a scan speed.

In further embodiments, the triggering events may be one or more of a trigger derived from a master clock, a trigger derived from the source of optical radiation, a trigger derived from the detection system, a trigger derived from the at least one steerable mirror, a trigger derived from an at least one second steerable mirror, a trigger derived from a motion sensor associated with the subject, and a trigger derived from an external device.

Related controllers and methods are also provided.

BRIEF DESCRIPTION OF THE DRAWINGS

FIG. 11 is a diagram illustrating a scan instruction and possible instruction opcode table in accordance with some embodiments of the present inventive concept.

DETAILED DESCRIPTION

Figure 1:
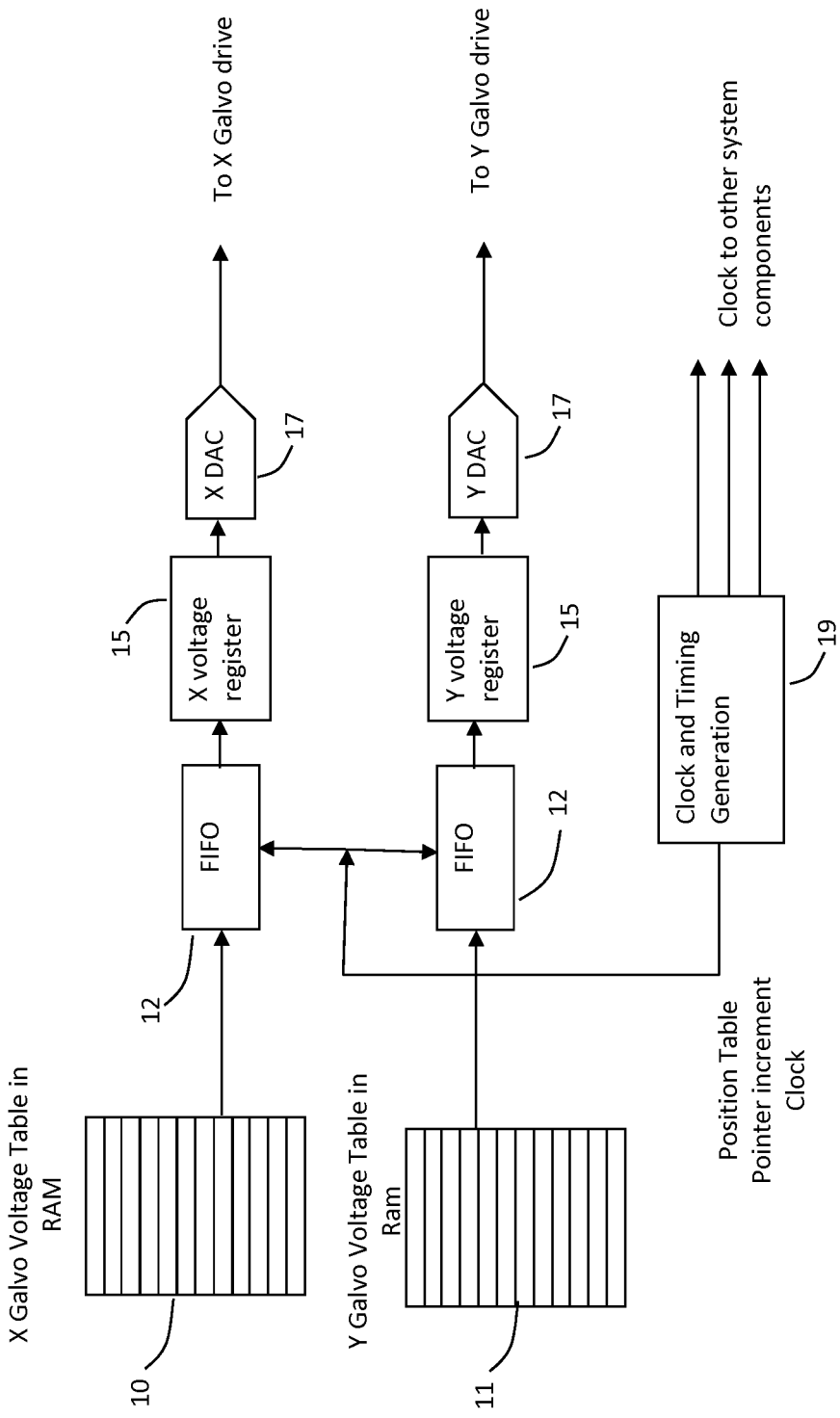
FIG. 1 is a block diagram illustrating a conventional optical scanning system including a pair of voltage tables stored into a memory buffer.

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

As discussed above, embodiments of the present inventive concept are directed to optical scanning systems. For example, some embodiments provide optical scanning systems that include a source of optical radiation, having one or more mirrors used to steer a beam of light to produce a desired pattern for various applications. Some embodiments of the present inventive concept relate particularly to overall system control, scan pattern generation, and synchronization of the various components of a scanning system. Embodiments of the present inventive are particularly relevant to optical scanning systems as applied to Optical Coherence Tomography (OCT) imaging systems, scanning laser ophthalmoscopes, and scanning confocal microscopes, and applications as will be discussed further herein with respect to FIGS. 1 through 13.

Some embodiments of the present inventive concept provide a scan controller platform specifically designed for optical beam scanning systems that additionally include detection systems for detecting optical radiation that interacts with or is returned from a subject, such as an optical coherence tomography (OCT) system, a scanning laser ophthalmoscope, or a scanning confocal microscopes and other such optical systems. As will be discussed herein, in some embodiments, the controller consists of three design layers, including a hardware platform, the field programmable gate array (FPGA) configuration, and firmware. On the hardware level in some embodiments the design includes a multi-channel galvo drive system, external trigger, scan failsafe circuit, optical scan elements actuator motor drives, remote slave controller, and a local user interface.

On the FPGA level, in some embodiments, the design includes a soft-processor, various peripheral blocks, a scan controller block, and a user interface block. The scan controller block of the present inventive concept consists of at least two distinct features. One feature may be computational pipeline to alter the table-prescribed scan pattern in real-time, and the other may be an instruction based real-time scan definition architecture.

On the firmware level, in some embodiments, the design consists of a multi-threaded embedded environment capable of monitoring the state of the system, processing commands from a host personal computer (PC), taking in command from the local user interface (UI), monitoring and controlling a remote slave controller, generating failure alarms and status updates to the host PC, keeping the local and remote control settings in sync, and the like.

Referring now to FIG. 1, as illustrated, in a conventional optical scanning system a pair of voltage tables (X Galvo and Y Galvo) are generated and stored into a memory buffer 10 and 11, respectively. A clock source 19 triggers the first in first out (FIFO) buffers 12 to update the X and Y digital to analog convertor (DAC) voltage registers 15 and to update the DACs 17, which in turn drive the mirror positioning galvos. At the next clock, the FIFO 12 sends out the next value in the queue until the table has reached the end, and the table is reloaded from the beginning. This may be done using, for example, generic data acquisition cards in a PC or a customized galvo drive DAC.

Embodiments of the present inventive concept include a fully integrated optical scanning drive system with actuator drives to control optical elements as well as multiple galvo drive channels. The actuators as well as the galvo drives are all controlled under a central FPGA System-on-a-Chip architecture, allowing for tightly coupled configuration and controls amongst the many system components. The FPGA provides precise timing and efficient computational pipeline, while the microcontroller allows for ease of programming and extensive command interface to an external host PC.

Figure 2:
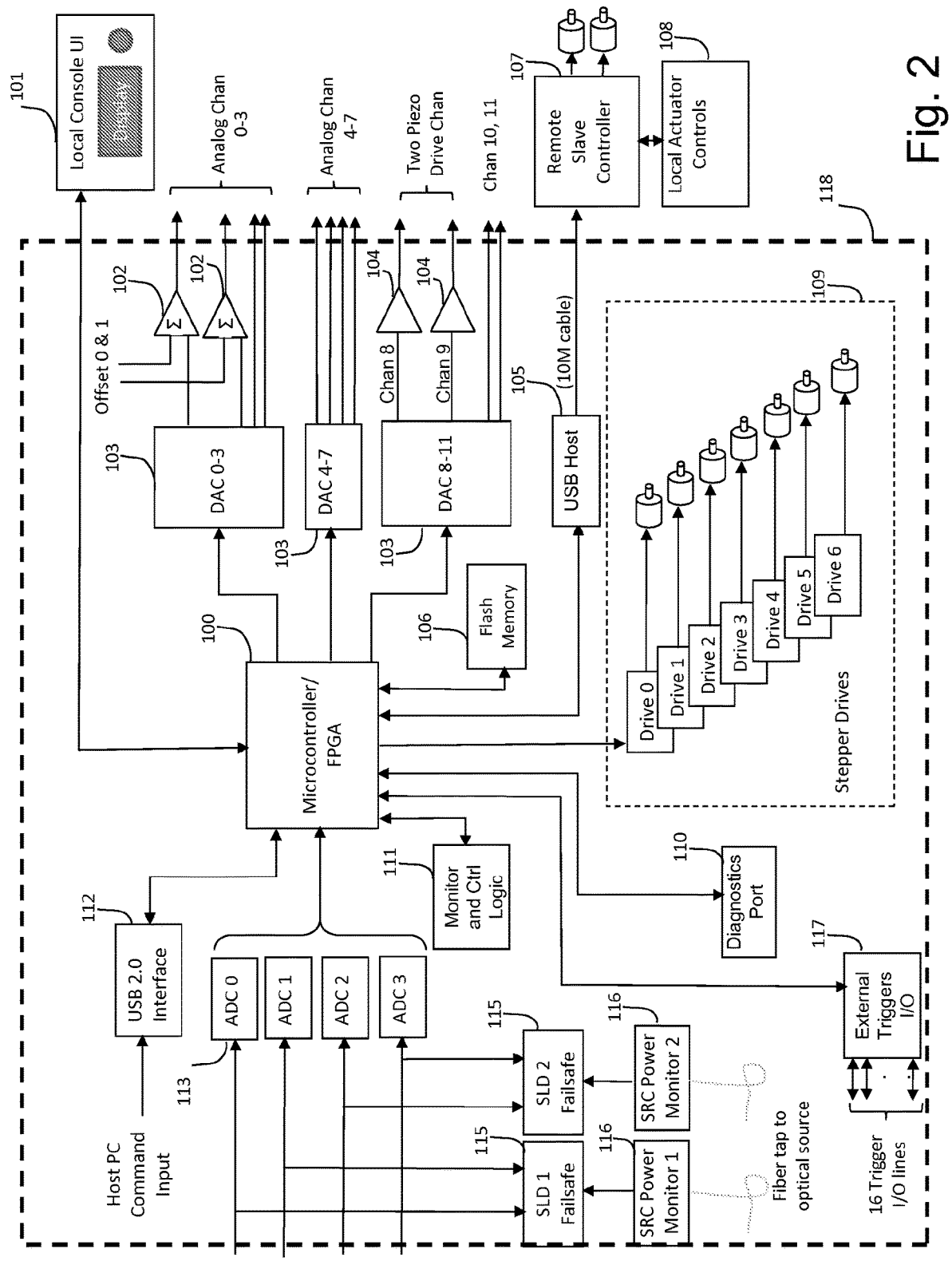
FIG. 2 is a block diagram illustrating high level controller hardware.

Referring to FIG. 2, a high level controller hardware block will be discussed. At the center of the controller is an FPGA module 100, which may be off the shelf, with all the supporting components to function as a microcontroller with many I/O lines for custom applications.

The FPGA Module

In some embodiments, the FPGA module 100 is plugged into a mother board 118 that consists of the specialized functional blocks. These functional blocks include, but are not limited to, digital-to-analog converters (DACs), analog-to-digital converters (ADCs), failsafe circuits, a universal serial bus (USB) host controller, a USB device controller, stepper motor drives, user interface port, external triggers I/Os, and the like.

As discussed above, the system may include one or more actuators. The one or more actuators may be configured to receive first and second instructions sets from the microcontroller and the FPGA, respectively. In some embodiments, the first instruction set may establish a pattern of motion of at least one steerable mirror at least partially responsive to inputs from the user interface of the communications device. The second instruction set may modify an attribute of the pattern of motion of the at least one steerable mirror in substantially real-time at least partially responsive to one or more triggering events. As used herein, "triggering events" refer to one or more of a trigger derived from a master clock, a trigger derived from the source of optical radiation, a trigger derived from the detection system, a trigger derived from the at least one steerable mirror, a trigger derived from an at least one second steerable mirror, a trigger derived from a motion sensor associated with the subject, and a trigger derived from an external device.

In some embodiments, the master clock may include a master clock of the controller and the trigger derived from the master clock may be one a series of clocks that generated in clock divider.

In some embodiments, a trigger derived from the source of optical radiation may be a trigger in response to a modulation signal of the optical source, a fault condition of the optical source, or a high or low power condition of the optical source. The optical source from which the trigger is derived may be the imaging source of optical radiation of the optical system, or in some embodiments the trigger may be derived from a different source of optical radiation. In the latter case, the source of optical radiation from which the trigger is derived may be a second source of optical radiation directed at the subject, and the trigger condition may include high power condition of this second source of optical radiation or may include the sums of the powers of the optical radiation from the second source and the scanning beam source of optical radiation.

In some embodiments, the trigger derived from the detection system may include the synchronous master clock of the detection system or an asynchronous signal delivered in response to a detection or fault condition of the detection system.

In some embodiments, the trigger may be derived from the steering mirror itself, such as fault condition or a limit condition returned from the steerable mirror or its actuator.

In some embodiments, the trigger may be derived from a second steering mirror, such as fault condition or a limit condition returned from the second steerable mirror or its actuator. In some embodiments the first steerable mirror moving in response to the trigger will be a "slow" mirror and the second mirror will be a "fast" mirror that provides a trigger at the limits of its scan range or some other condition defined by its scanning.

In some embodiments, the trigger will be derived from a motion sensor associated with the subject. The motion sensor may be an accelerometer, and the trigger may be indicative of a motion of a degree of motion of the subject, and the response conveyed to the actuator may be to direct the steerable mirror to maintain an aiming of the source of optical radiation at substantially fixed position with respect to the subject.

In some embodiments, the trigger will be derived from an external signal that may include detection of instrument or foreign body with an instruction set to the steerable mirror to track or avoid the instrument or the foreign body.

In some embodiments, the trigger will be derived from a user interface and include real-time feedback from a user to the system through concurrent instruction set of the FPGA.

In some embodiments, the second instruction set from the FPGA may be configured to execute the first instruction set from the microcontroller directly. In further embodiments, the second instruction set may be configured to modify one or more of a scan scale, a scan rotation angle, a scan location, a scan correction to a beam position from optical distortion or scanning system mechanical nonlinearities, a scan start time, a scan stop time, and a scan speed.

Digital to Analog Converters

In some embodiments, the DAC block 103 consists of up to twelve analog output channels, arranged in groups of 4 channels per block. These may be 16 bit DACs, capable of sample rates of up to 500 Ks/sec. The FPGA is configured to update the DAC devices synchronous to an internal or external trigger source. The output of the first two channels of the twelve includes an analog signal adder 102 in order to allow an external beam steering signal. This feature enables an external control system, such as instrument tracking, to steer the beam to a desired coordinate.

Channels eight through 11 are intended for piezo drive and phase stepping applications. Two of the four of this DAC bank are equipped with power amplifier 104 drivers capable of directly driving piezo devices. In some embodiments, a daughter card may be added to provide voltage step up circuit to allow the piezo amplifiers to operate at higher voltages.

Analog to Digital Converters

The Analog to Digital Converters (ADC) block 113 includes up to four analog inputs, used to monitor the galvo actual position feedback. The serial output data from the ADC devices is directly accessible to the FPGA, which can monitor and store them into memory as required.

Failsafe System

Figure 3:
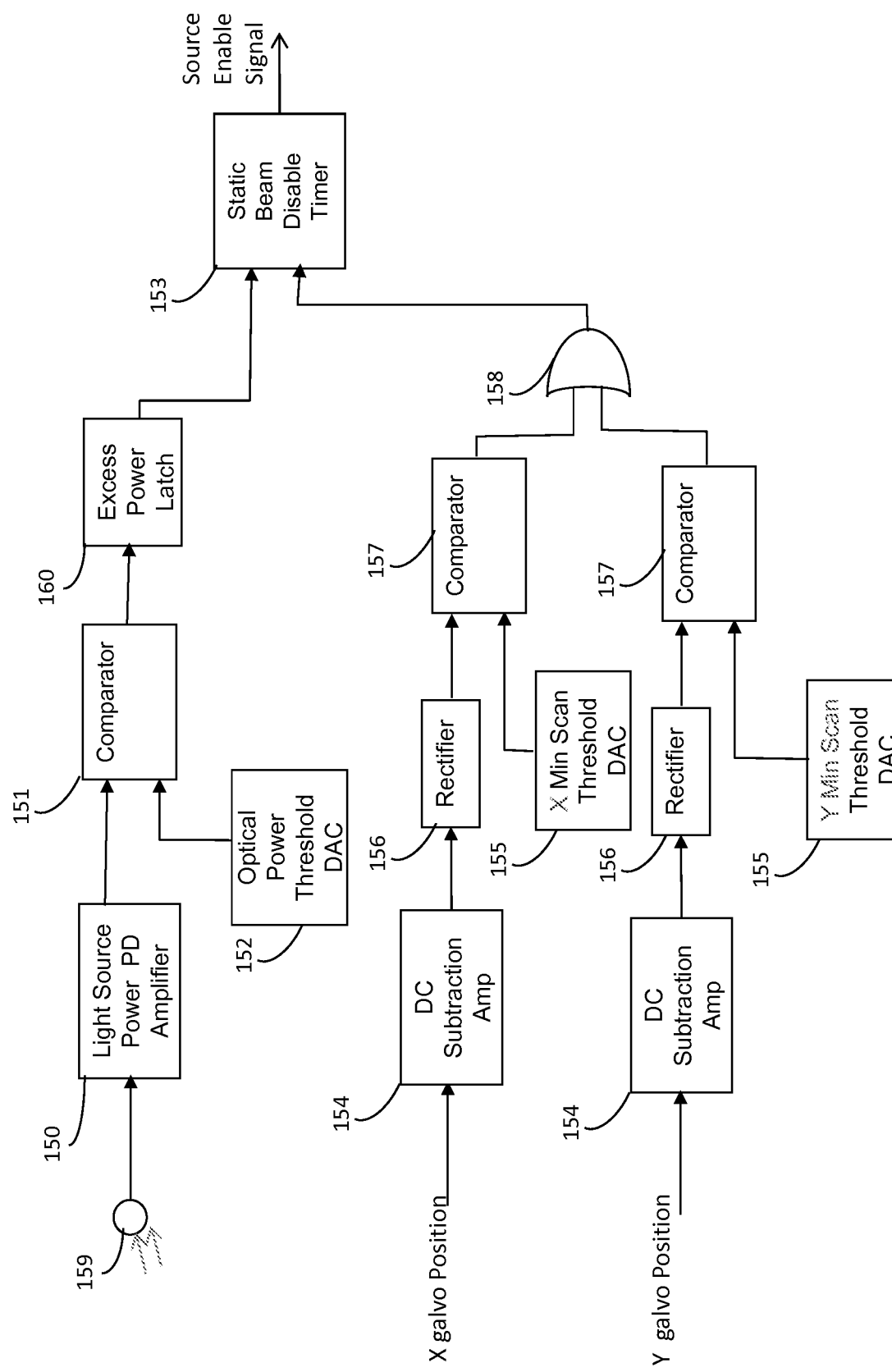
FIG. 3 is a block diagram illustrating a passive failsafe in accordance with some embodiments of the present inventive concept.

As part of an opthalmological application of a beam scanning system, such as OCT, a failsafe circuit ensures that the scanning beam power is first of all within safe limits, and second that the beam is not allowed to stay static in one spot causing unintended exposure to the tissue. The controller described herein includes a passive failsafe 115 that works independent from the FPGA, but includes the capability to have the limit thresholds to be adjusted via firmware. As illustrated in FIG. 3, the failsafe circuit operates by detecting the x and y galvo position signals and ensuring that the motion is above a set threshold. The position feedback from the galvo drive amplifiers are processed by a low pass filter with break frequency near DC 154. This feature reduces, or possibly eliminates, the failsafe dependency on absolute galvo position and reacts to relative galvo motion, which is the intended function. In scenarios where a small scan is steered in one of the four quadrants, away from the origin, the failsafe functions just the same.

The output from the DC subtraction amplifies are rectified 156 to convert the bipolar signal to a positive only signal. The positive signal representing the galvo motion is compared 157 with a preset threshold 155 to generate a logic signal. The same signal is generated for the second channel and fed to a logical OR device 158. This arrangement allows for either the x or y channel activity to reduce the likelihood, or possibly prevent, a static beam disable timer 153 to timeout and disable the light source.

The failsafe circuit also includes a SLD/Laser source power monitoring capability where a photodiode 159 samples a fraction of the scan beam and after amplification 150, using a comparator 151, and it is compared against a safe limit reference voltage. In the unlikely event the power exceeds the set threshold, the excess power latch 160 is set, activating the static beam disable timer.

Stepper Drive Circuit

The controller is equipped with seven stepper drive circuits 109, all controlled via a serial communication channel from the FPGA. The stepper drives are intended to drive an optical component of the scanning system such as reference arms, polarization, reference arm attenuation, focus, alignment, and the like. There are up to eight switch inputs to detect the actuator position limits as a mean to initialize and home the actuators. Other methods of absolute position detection are also possible through either serial communication channels provided on the controller.

Local Console User Interface (UI)

The controller interfaces with an external low resolution, monochrome, display 101 to allow local control and monitoring of system actuators and devices. The user interface 101 includes a rotary encoder for user input.

External Trigger

Synchronization with external devices may be achieved via a 16 channel trigger I/O interface 117. The trigger signal directions are software configurable, allowing an array of system configuration permutations.

Diagnostics Port

A local diagnostic 110 port provides easy access to the system status via firmware commands.

USB 2.0 Interface

The USB device port 112 is the primary means of control and communication between the controller and the host PC. The USB 2.0 device interfaces with the FPGA through a 16-bit parallel bus allowing fast data exchange between the controller and the PC. In addition, the USB 2.0 controller allows FPGA bit-stream and firmware updates in the field.

Remote Slave Controller

In many applications the scan head is not co-located with the scan engine. In such embodiments there are active components, such as actuators or local light sources that will need to be controlled from the host PC or the scan controller. Some embodiments include an interface to accommodate for a remote slave controller 107. The remote slave controller may consist of two stepper motor based actuators for adjustment of focus and numerical aperture of the beam at the sample. The remote slave controller also includes a control panel 108 with two rotary encoders to allow local adjustment of the actuators.

USB Host Controller

The scan controller design includes a USB host controller 105 with two ports to provide a communication channel for up to two remote slave controllers and the scan controller. The choice of USB bus allows for the remote slave controller to be used standalone with a PC if desired. In order to extend the range of USB maximum allowable cable length, a USB over Cat5 device is incorporated.

On Board Flash

In addition to the 16 MB of flash available on the FPGA module for firmware and FPGA bit stream, in some embodiments, the boards include 8 MB of flash and 128 KB of EEPROM on the motherboard 106. These memory devices allow for storage of system settings and calibration data if required.

FPGA Configuration

Figure 4:
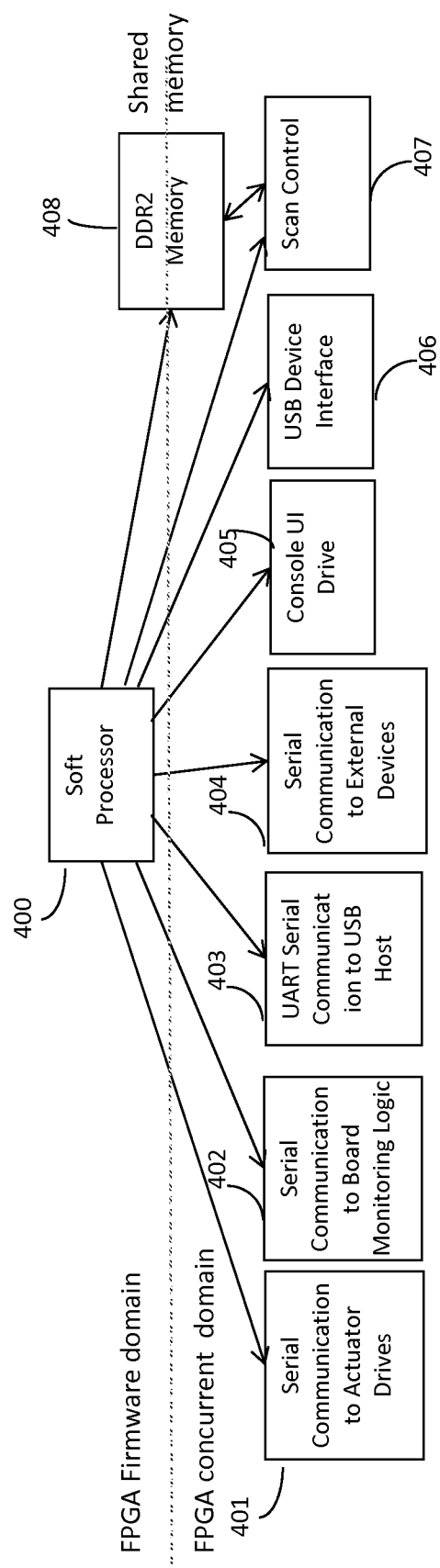
FIG. 4 is a block diagram illustrating a field programmable gate array (FPGA) in accordance with some embodiments of the present inventive concept.

An FPGA internal functional block in accordance with some embodiments of the present inventive concept will now be discussed with respect to FIG. 4. The FPGA is internally configured to include a soft-processor 400 as the microcontroller platform for firmware development. There are a series of generic peripheral IP modules that communicate with the external devices. These may include, for example, the serial communication modules 401, 402, 403, and 404. Module 405 is a custom block (console user interface (UI) drive) developed to communicate with the display device and a filtered quadrature decoder to filter noise and convert encoder signal to user input for the firmware. The software processor 400 further communicates with a universal serial bus (USB) device interface 406, a scan control module 407 and a DDR2 Memory 408 in accordance with some embodiments of the present inventive concept.

Scan Control Block

Figure 5:
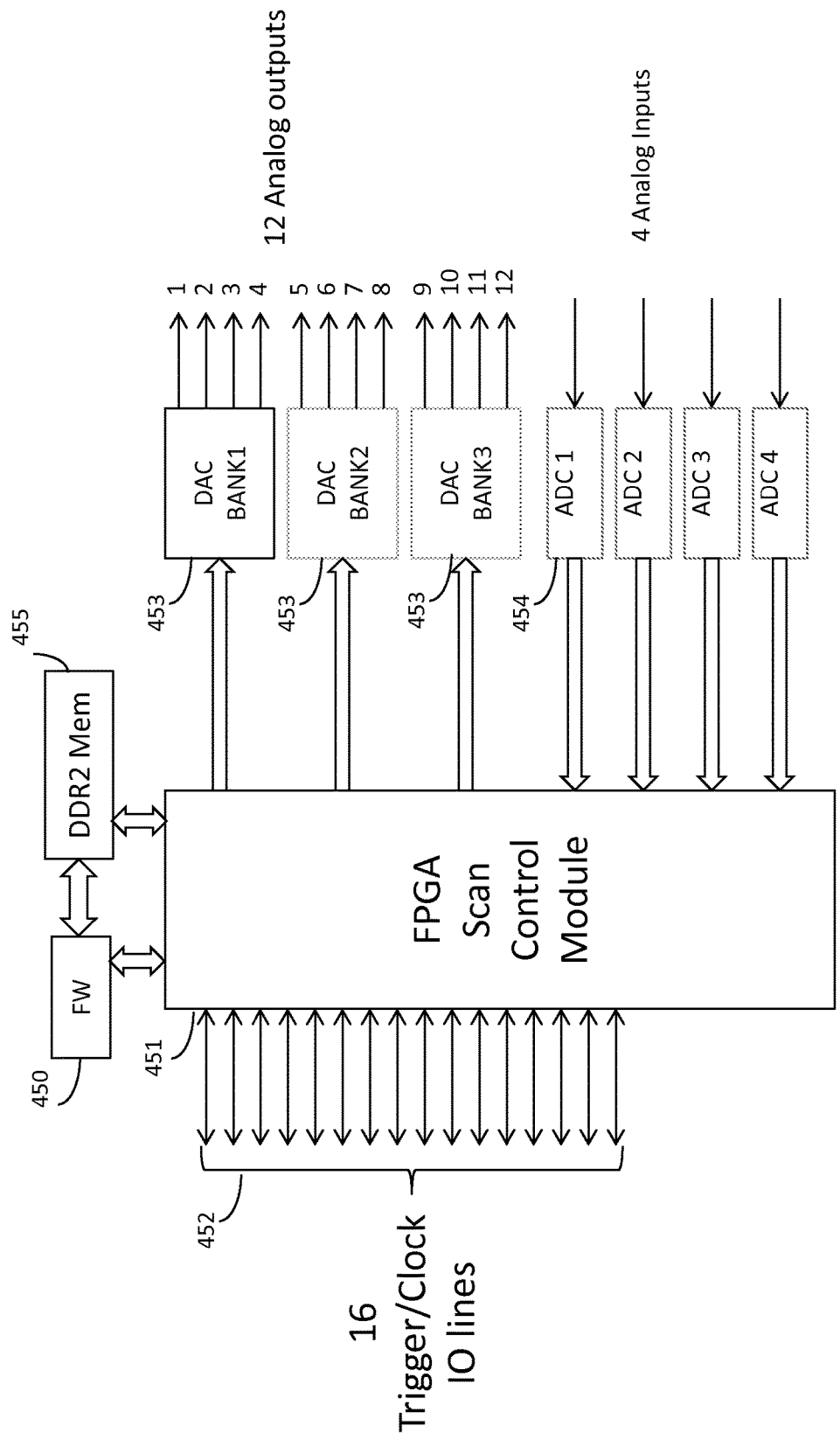
FIG. 5 is a block diagram illustrating a scan control block in accordance with some embodiments of the present inventive concept.

Referring now to FIG. 5, the scan control block 451 may allow for up to 16-trigger input/outputs 452 and may drive three banks of DACs, each having four channels of output 453. It can also simultaneously read from the four ADC devices 454 (ADC1, ADC2, ADC3 and ADC4). The scan control block 451 includes direct memory 455 access mechanism to allow low latency access to data and be able to write data back into the memory independent form the FW. The firmware 450 has register access to the scan control block, allowing it to configure the block parameters and read back the status of the module.

Figure 6:
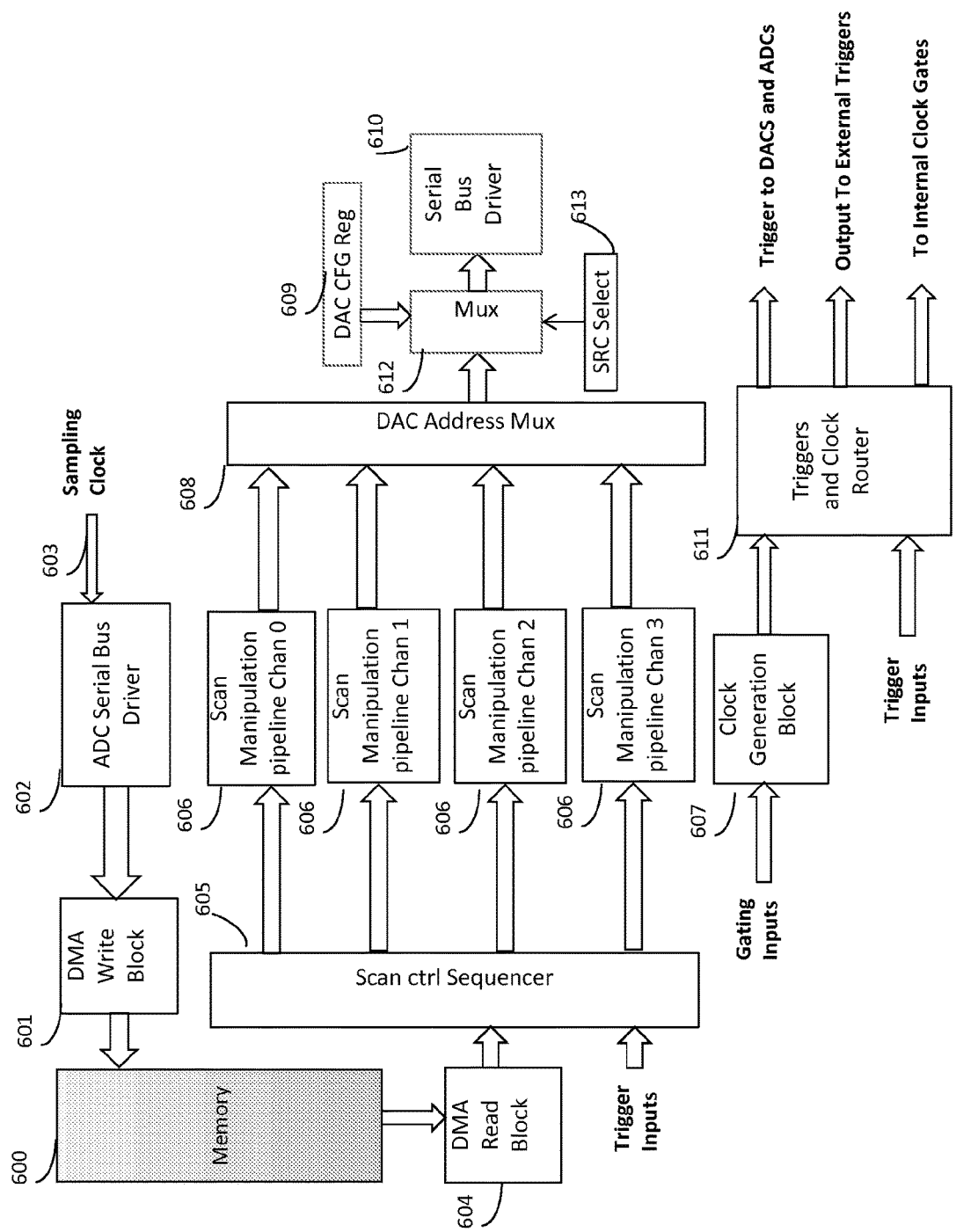
FIG. 6 is a block diagram illustrating a scan control block in accordance with some embodiments of the present inventive concept.

Referring now to FIG. 6, the scan control block consists of a DMA logical block 604 to read data from a given memory pointer location and pass on to the DAC output sequencer 605. Each DAC channel can be run independently at a different trigger or clock rates. The sequencer block 605 keeps track of a trigger signal for each channel and requests for the next data from the DMA block once it has outputted the current cached data. The data for each channel is fed into the respective pipeline and is passed on to the DAC address multiplexer block 608 once processed. The DAC address multiplexer block forms the command for the external DAC chip and sends the data to the serial bus driver. The output sample rate is in the order 100s of KHz, much lower than the FPGA system clock of 100 MHz or more. Typical DMA access and pipeline processing delays are much shorter that the DAC sample rate and does not cause any unwanted latency in DAC outputs. The data multiplexer 612 allows for direct FW access to the DAC through a memory mapped register 613. This feature can be used to initialize and configure the DACs, and may also be used for firmware based sample outputs, if required.

Figure 7:
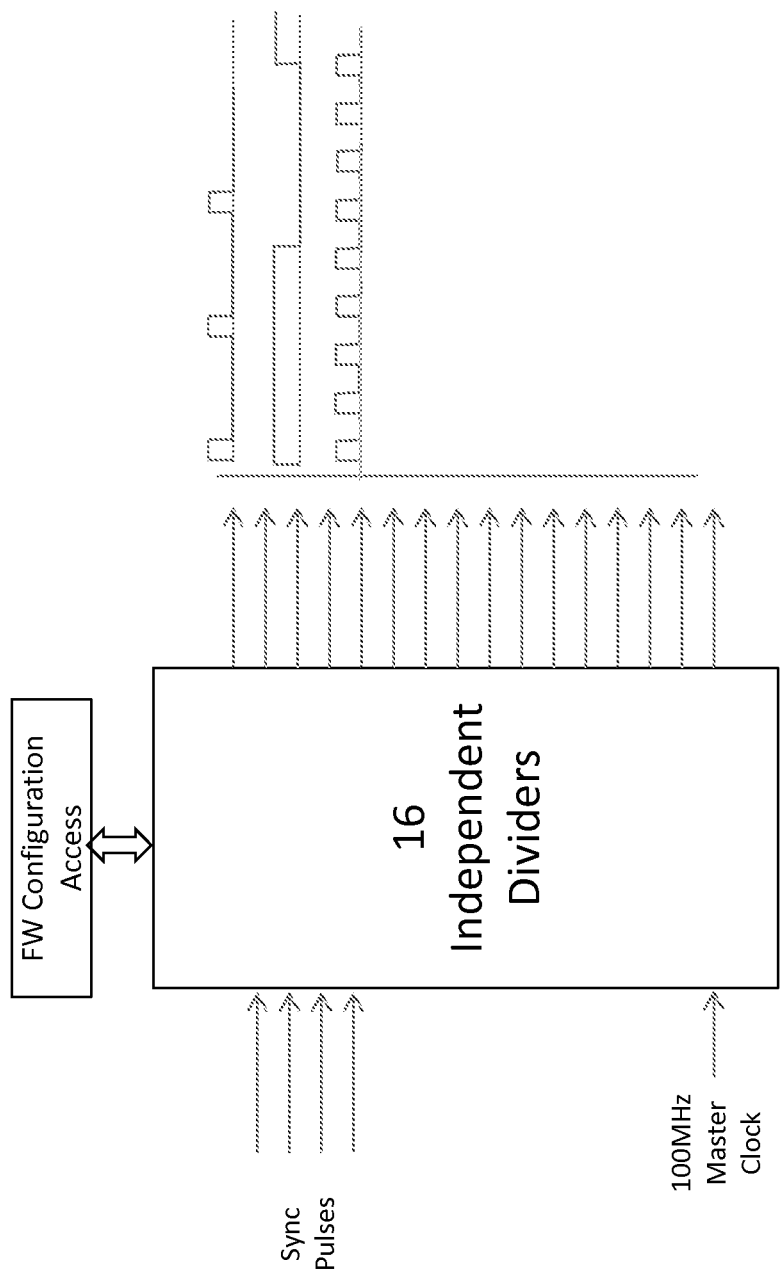
FIG. 7 is a block diagram illustrating a clock generation block generating up to 16 clocks from the system 100 MHz clock.
Figure 8:
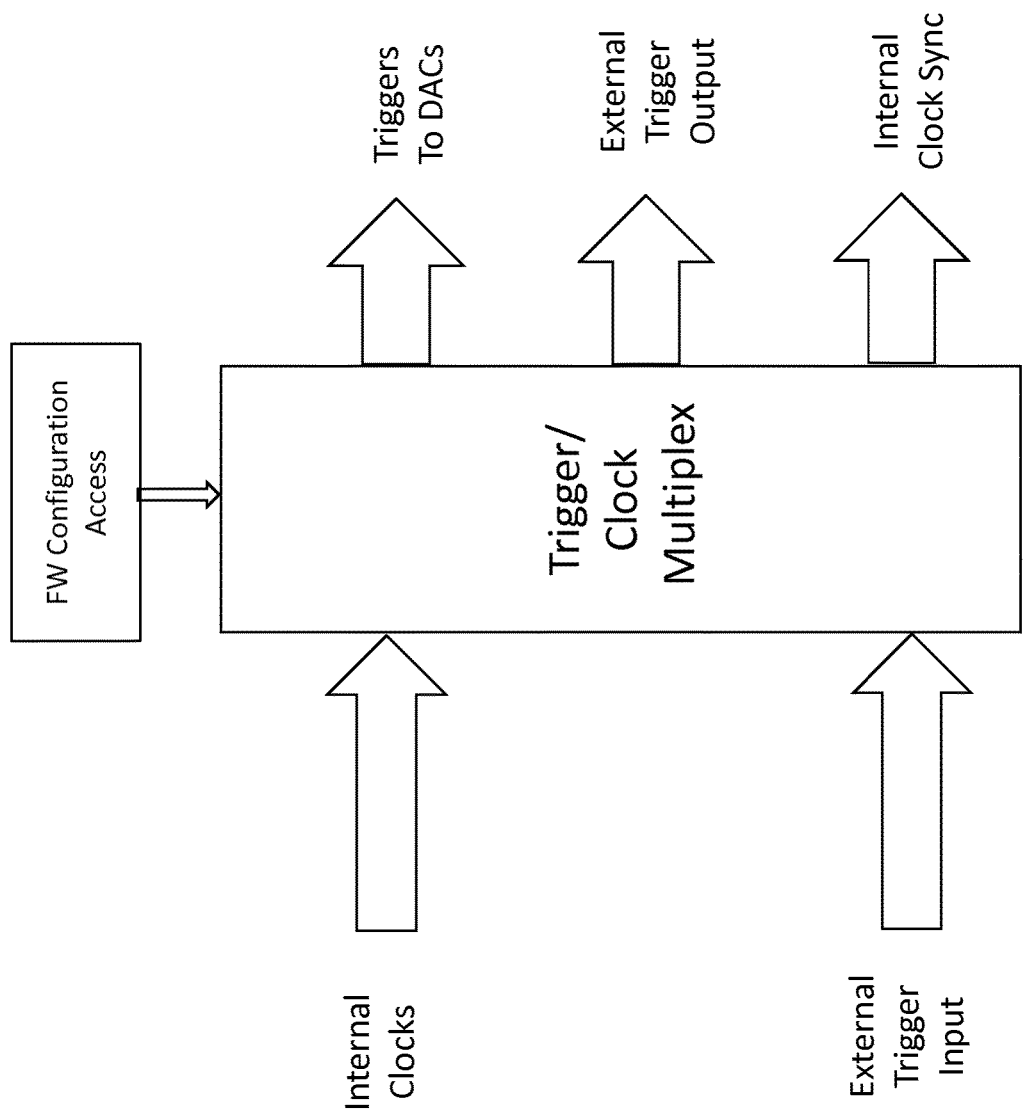
FIG. 8 is a block diagram illustrating various triggers/clocks in accordance with some embodiments of the present inventive concept.

A clock generation block 607 receives gating inputs as illustrated in FIG. 6. The clock generation block 607 may be implemented to generate up to 16 clocks from the system 100 MHz clock as illustrated in FIG. 7. Each clock duty cycle can be independently configured. A trigger and clock router block 611 (FIG. 6) allows for software configurable trigger and clock routing to different parts if the scan control block. External input triggers can be routed to drive the DACs, to initiate ADC sampling, or to gate an internal clock. Internal triggers or clocks can be routed out to any of the trigger lines for external devices as illustrated in FIG. 8.

The ADCs can operate in parallel with the DACs with the ADC serial bus driver 602 sampling the galvo position data when triggered by sampling clock 603. The data from the ADCs can then be directly written to the system memory by the DMA write block 601.

Figure 9:
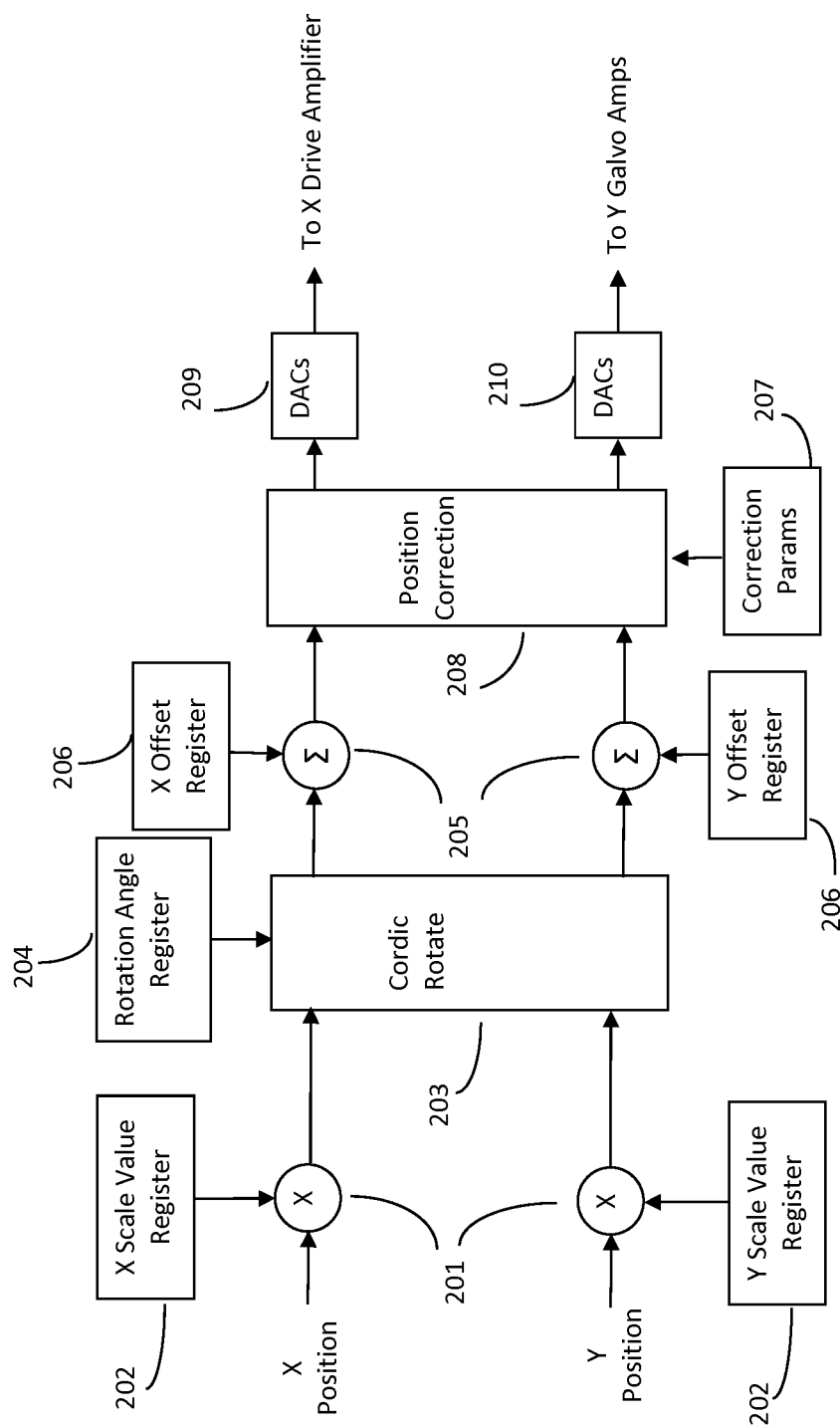
FIG. 9 is a block diagram illustrating a scan control pipeline in accordance with some embodiments of the present inventive concept.

As illustrated in FIG. 9, in some embodiments, the scan control pipeline consists of scaling operation 201 value set by firmware into X or Y scale value register 202. The scan coordinate location can be rotated using a Coordinate Rotation Digital Computer (Cordic) module 203. The rotational angle may be set by firmware access into the rotation angle register 204. The scan coordinates can be translated in x or y direction in offset stage 205, with firmware access into the x/y offset register 206.

The scan manipulation pipeline also includes a scan position correction block 208 that allows for correction to the beam position that may stem from optical distortion or scanning system mechanical nonlinearities. This correction can either be computational or table lookup based. The correction parameters may be set via firmware access to correction parameters (params) register 207. As illustrated in FIG. 9, the position correction information 208 may be provided to the DACs 209, 210 couples to the X and Y galvo amplifiers, respectively.

To enhance the capability and flexibility of the scan control block, a secondary table, in parallel with the galvo voltage table, may be provided in accordance with some embodiments of the present inventive concept. The secondary table consists of predefined scan modifier instructions, which may include scan-manipulation-pipeline parameter update or scan table sequence modifier instructions. This feature works much like a microprocessor instruction set, providing means to update special registers, loops, and the like. The key requirement is to keep up with the scan DAC update clock.

Figure 10:
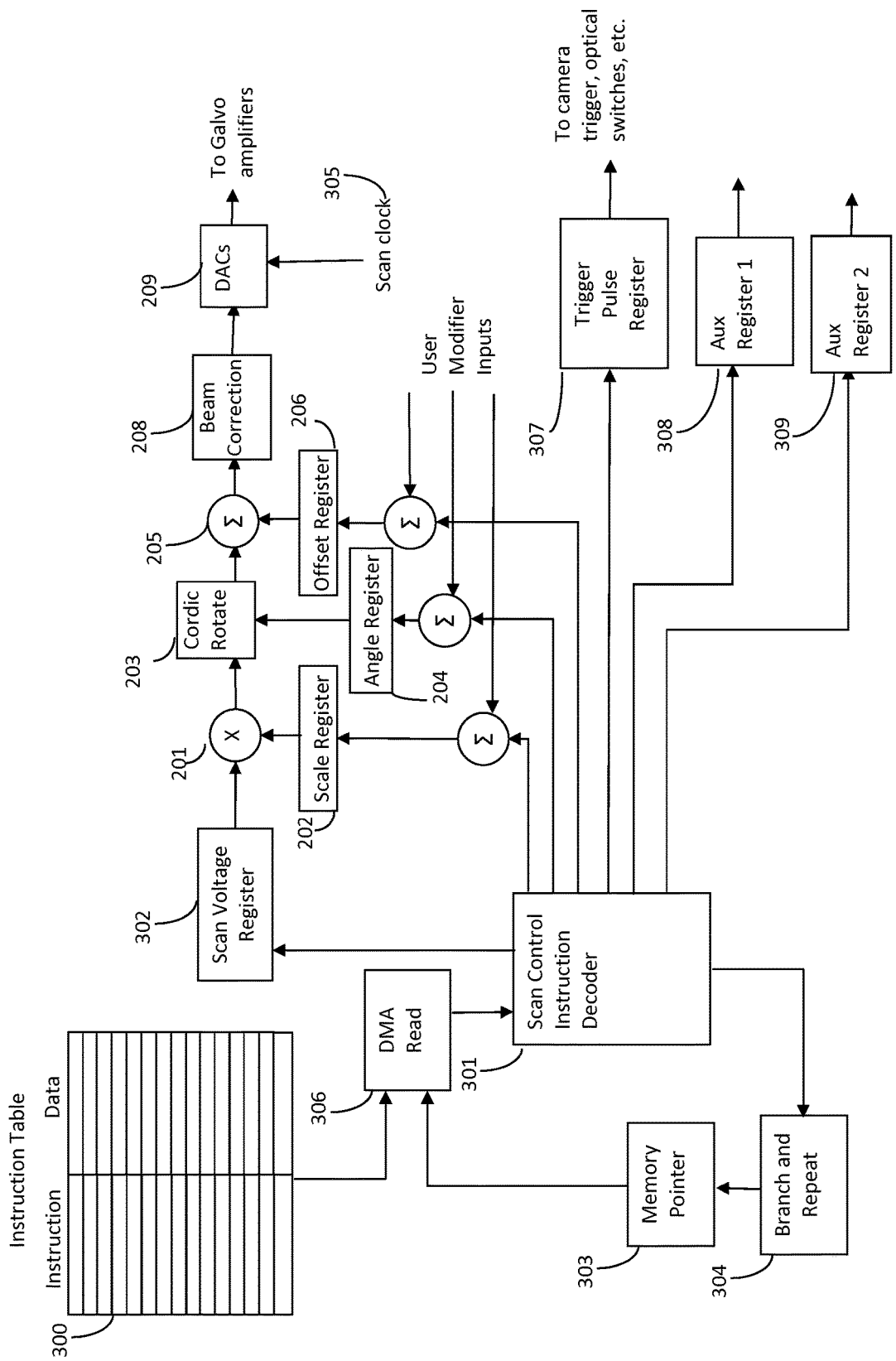
FIG. 10 is a block diagram illustrating a configuration for the instructional scan concept for one channel in accordance with some embodiments of the present inventive concept.

Referring now to FIG. 10, a configuration for the instructional scan concept for one channel, which can be extended to include others, will be discussed. It will be understood that the configuration of FIG. 10 is provided for exemplary purposes only and that embodiments of the present inventive concept are not limited to this configuration. As illustrated in FIG. 10, the scan instruction table 300 is stored in the system memory and consists of a data field and an instruction field. The DMA read block 306 fetches the instruction and the corresponding data fields from memory location provided by the memory pointer register 303 and feeds the values to the scan control instruction decoder 301. The instruction decoder 301 evaluates the instruction field and determines if the data field is the DAC next voltage value, in which case it updates the scan voltage register 302. If the instruction indicates a pipeline parameter modifier such as scaling 201, rotation 203, or offset 205, the decoder updates the corresponding scale register 202, angle register 204, and offset register 206, respectively.

This scheme can also include arbitrary digital signal generator, in sync with the DAC voltage outputs. The instruction field may include command to update the trigger pulse register 307 that may be routed to any of internal or external trigger lines.

The instruction code may also include one or more auxiliary digital data registers, such as 308 and 309. These registers may be used, for example, to drive another DAC that is attached to a light source power control, an optical element actuator, an X-Y stage, and the like.

Optical scan schemes, such as radial, raster patterns, or annular, often consists of repeat of a sequence followed by increment of some parameter. For example in a raster pattern for a given y coordinate, the x channel is advanced through a sequence of n steps from a start value to an end value, which may include a desired fly-back trajectory. The pattern is repeated again with y value incremented from an initial value to some maximum value and then back to the start value. Similar behavior applies to radial scan, in which case x and y values are set to produce a line as in diameter of a circle followed by a desired fly back trajectory, the pattern is then repeated with the angle of the line incremented by some value. In polar coordinate, this is simply an increment in angle $\theta$ with radius kept constant. Radial scan also similar behavior, this time the radius is incremented.

Using embodiments discussed herein, a simple pipeline parameter modify instruction followed by a pointer modify instruction can greatly reduce the memory required to store the data for a volume scan in case of an OCT system. This may also reduce the time necessary to download and store the instruction into the system memory. The raster scan is simply a pipeline offset increment instruction, the radial scan is rotation angle increment, and annular scan is scale increment.

In some embodiments, the parameter increment instruction may include a means to specify the start value, end value, and increment step value. These values can be specified as consecutive instructions in the table. The typical system clock being much higher than the mirror position update rate, several instructions can be fetched from memory and processed in between DAC sample updates.

Referring now to FIG. 11, a diagram illustrating an example scan instruction and possible instruction opcode table will be discussed. Although only one byte is allocated for the instruction, allowing up to 256 possible instruction codes in FIG. 11, embodiments of the present inventive concept are not limited to this configuration. For a 32-bit data and instruction field per table entry, 16 bits of data field is sufficient for the DAC voltage, scale, offset, and angle specifications. The instruction code can be placed in the most significant byte (MSB) of the 32-bit filed. For larger data fields either the three MSBs after the instruction field may be used, of a consecutive memory access may be employed.

Figure 12B:
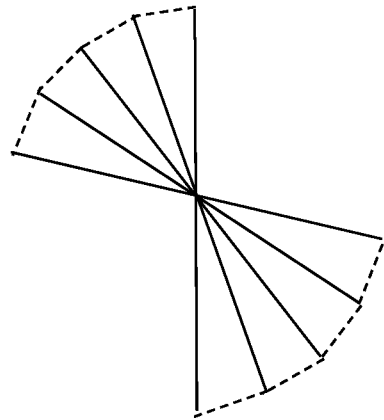
FIGS. 12A and 12B are a table and a diagram illustrating example operations in accordance with some embodiments of the present inventive concept.
Figure 12A:
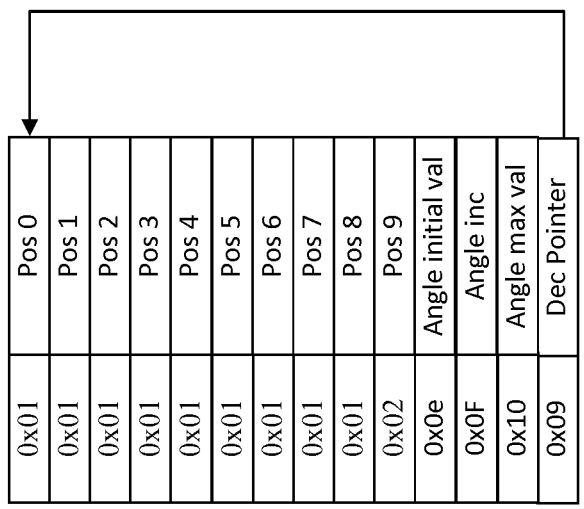

Referring now to FIG. 12, an example scenario will now be discussed. To generate a radial volume pattern, a scan progression for one angle is generated followed by the initial angle value, increment steps, and maximum angle value. At the end of the table a pointer decrement instruction is placed to loop back to the beginning of the table. As the DAC scan clock 305 in FIG. 10 triggers the DAC output block 209 and the voltages are output, the next voltage is fetched from the instruction table. Once the angle manipulation instructions are encountered the decoder block 301 of FIG. 10, compares the current rotation angle register 204 with the maximum allowed value in the instruction if not exceeded it increments the angle register with the increment amount. The pointer modifier branches back to the beginning of the table and the process repeats, generating a radial volume scan. This is essentially a specialized while loop in computer programming language, specific to scan control.

Thus, for a 1000×1000 rectangular scan, this can significantly reduce the table data transfer time and memory usage. For a 16-bit DAC system, this would result in 4 megabytes of data. Whereas using the scheme presented here the data usage drops down to slightly above 4 kilobytes of data.

Random/Hardware Pattern Generator

Figure 13:
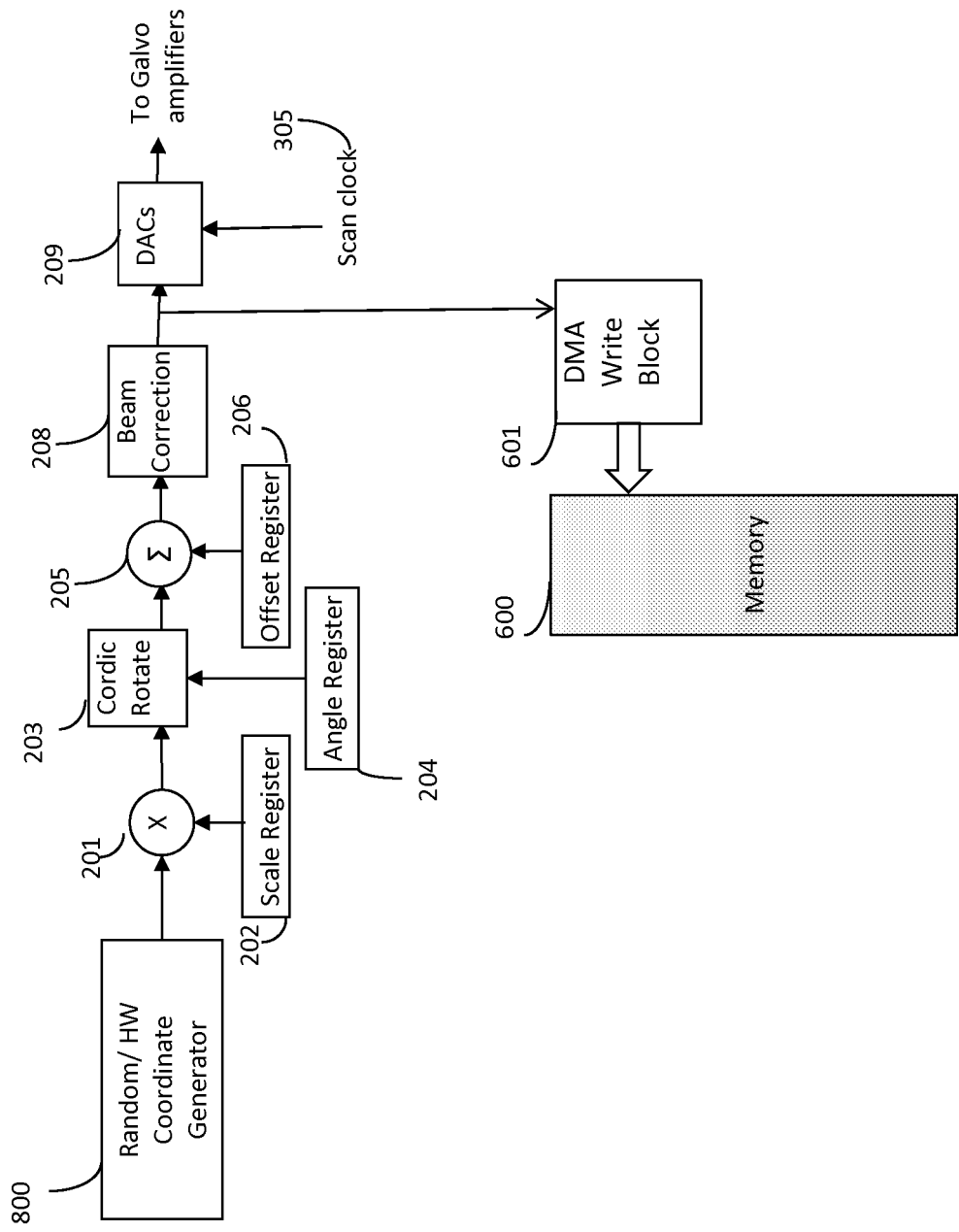
FIG. 13 is a block diagram illustrating a hardware pattern in accordance with some embodiments of the present inventive concept.

Referring now to FIG. 13, a block diagram of a random/pseudorandom 800 or a structured hardware pattern generator FPGA block used to drive mirror positions will be discussed. To provide the image processing software with the mirror positions, a DMA write block 601 as shown in FIG. 13 may be configured. As each DAC is updated with a new value, the value is captured and put into the controller memory 600. Details with respect to blocks 201, 202, 203, 204, 205, 206, 208, 209 and 305 are discussed above and will not be repeated herein in the interest of brevity. Partial and full table values can then be retrieved by the image processing software to correlate the camera images with galvo mirror positions.

Example embodiments are described above with reference to block diagrams and/or flowchart illustrations of methods, devices, systems and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, example embodiments may be implemented in hardware and/or in software (including firmware, resident software, micro-code, etc.). Furthermore, example embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of example embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a field programmable gate array (FPGA), or a programmed digital signal processor, a programmed logic controller (PLC), or microcontroller.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed exemplary embodiments of the inventive concept. However, many variations and modifications can be made to these embodiments without substantially departing from the principles of the present inventive concept. Accordingly, although specific terms are used, they are used in a generic and descriptive sense only and not for purposes of limitation, the scope of the inventive concept being defined by the following claims.

What is claimed is:

1. A scanning optical system comprising:
a source of optical radiation;
an optical scanning beam delivery system for delivering optical radiation to a subject, wherein the optical scanning beam delivery system includes a plurality of optical elements including at least one steerable mirror;
at least one actuator coupled to the at least one steerable mirror,
a detection system for detecting optical radiation returned from a subject;
a communications device including a user interface and configured to process a set of instructions at least partially responsive to inputs from the user interface;
a controller comprising memory, a microcontroller and a field programmable gate array (FPGA), the microcontroller and FPGA receiving instructions derived from the communications device; and at least one actuator coupled to the at least one steerable mirror, wherein the at least one actuator receives a first instruction set from the microcontroller in a form of sequential commands and a second instruction set from the FPGA in a form of concurrent commands;

wherein the first instruction set establishes a pattern of motion of the at least one steerable mirror at least partially responsive to inputs from the user interface of the communications device;

wherein the second instruction set modifies an attribute of the pattern of motion of the at least one steerable mirror in substantially real-time at least partially responsive to one or more triggering events; and wherein the first and second instruction sets are applied to a plurality of two-dimensional coordinates (X, Y) to alter a scan pattern in real time.

2. The system of claim 1, wherein the microcontroller is a soft-processor configured within the FPGA.

3. The system of claim 1, wherein the system is one of an optical coherence tomography imaging system, a scanning laser opthalmoscope, and a scanning confocal optical microscope.

4. The system of claim 3, wherein the microcontroller populates a table in the memory of the controller with the first instruction set.

5. The system of claim 4, wherein the FPGA is configured to execute the instructions in the memory of the controller responsive to the second instruction set.

6. The system of claim 5, wherein the second instruction set executes the first instruction set directly or modifies one or more of a scan scale, a scan rotation angle, a scan location, a scan correction to a beam position from optical distortion or scanning system mechanical nonlinearities, a scan start time, a scan stop time, and a scan speed.

7. The system of claim 6, wherein the triggering events comprise one or more of a trigger derived from a master clock, a trigger derived from the source of optical radiation, a trigger derived from the detection system, a trigger derived from the at least one steerable mirror, a trigger derived from an at least one second steerable mirror, a trigger derived from a motion sensor associated with the subject, and a trigger derived from an external device.

8. A controller for a scanning optical system, the controller comprising:

a memory;

a microcontroller coupled to the memory; and a field programmable gate array (FPGA) coupled to the memory and the microcontroller, wherein the microcontroller and FPGA receive instructions derived from a communications device, wherein the communications device includes a user interface and is configured to process a set of instructions at least partially responsive to inputs from the user interface and wherein the optical system comprises:

a source of optical radiation;

an optical scanning beam delivery system for delivering optical radiation to a subject, wherein the optical scanning beam delivery system includes a plurality of optical elements including at least one steerable mirror;

at least one actuator coupled to the at least one steerable mirror;

a detection system for detecting optical radiation returned from a subject;

at least one actuator coupled to the at least one steerable mirror, wherein the at least one actuator receives a first instruction set from the microcontroller in the form of sequential commands and a second instruction set from the FPGA in the form of concurrent commands;

wherein the first instruction set establishes a pattern of motion of the at least one steerable mirror at least partially responsive to inputs from the user interface of the communications device;

wherein the second instruction set modifies an attribute of the pattern of motion of the at least one steerable mirror in substantially real-time at least partially responsive to one or more triggering events; and wherein the first and second instruction sets are applied to a plurality of two-dimensional coordinates (X, Y) to alter a scan pattern in real time.

9. The controller of claim 8, wherein the microcontroller is a soft-processor configured within the FPGA.

10. The controller of claim 8, wherein the system is one of an optical coherence tomography imaging system, a scanning laser opthalmoscope, and a scanning confocal optical microscope.

11. The controller of claim 10, wherein the microcontroller populates a table in the memory of the controller with the first instruction set.

12. The controller of claim 11, wherein the FPGA is configured to execute the instructions in the memory of the controller responsive to the second instruction set.

13. The controller of claim 12, wherein the second instruction set executes the first instruction set directly or modifies one or more of a scan scale, a scan rotation angle, a scan location, a scan correction to a beam position from optical distortion or scanning system mechanical nonlinearities, a scan start time, a scan stop time, and a scan speed.

14. The system of claim 13, wherein the triggering events comprise one or more of a trigger derived from a master clock, a trigger derived from the source of optical radiation, a trigger derived from the detection system, a trigger derived from the at least one steerable mirror, a trigger derived from an at least one second steerable mirror, a trigger derived from a motion sensor associated with the subject, and a trigger derived from an external device.

15. A method for controlling a scanning optical system, the system including a source of optical radiation; an optical scanning beam delivery system for delivering optical radiation to a subject, the optical scanning beam delivery system including a plurality of optical elements including at least one steerable mirror; at least one actuator coupled to the at least one steerable mirror; a detection system for detecting optical radiation returned from a subject; a communications device including a user interface; a controller comprising memory, a microcontroller and an field programmable gate array (FPGA), the microcontroller and FPGA receiving instructions derived from the communications device; and at least one actuator coupled to the at least one steerable mirror, the method comprising:

processing a set of instructions at least partially responsive to inputs from the user interface at the communications device;

receiving, at the at least one actuator, a first instruction set from the microcontroller in a form of sequential commands; and receiving, at the at least one actuator, a second instruction set from the FPGA in a form of concurrent commands, wherein the first instruction set establishes a pattern of motion of the at least one steerable mirror at least partially responsive to inputs from the user interface of the communications device;

wherein the second instruction set modifies an attribute of the pattern of motion of the at least one steerable mirror in substantially real-time at least partially responsive to one or more triggering events; and wherein the first and second instruction sets are applied to a plurality of two-dimensional coordinates (X, Y) to alter a scan pattern in real time.

* * * * *

UNITED STATES PATENT AND TRADEMARK OFFICE
CERTIFICATE OF CORRECTION

PATENT NO. : 10,791,255 B2
APPLICATION NO. : 15/523002
DATED : September 29, 2020
INVENTOR(S) : Mehran Ghofrani, Al-Hafeez Z. Dhalla and Christopher Saxer Page 1 of 1

It is certified that error appears in the above-identified patent and that said Letters Patent is hereby corrected as shown below:

On the Title Page

Item (54) and in the Specification, Column 1, Lines 1-2, In the Title:
Please change "SYTEMS" to -- SYSTEMS --.

Signed and Sealed this
Third Day of November, 2020

Andrei Iancu
*Director of the United States Patent and Trademark Office*